United States Patent [19]

Mechanic

[11] Patent Number: 5,332,475
[45] Date of Patent: Jul. 26, 1994

[54] CROSS-LINKING COLLAGENOUS PRODUCT

[75] Inventor: Gerald L. Mechanic, Chapel Hill, N.C.

[73] Assignee: University of North Carolina at Chapel Hill, Chapel Hill, N.C.

[21] Appl. No.: 849,898

[22] Filed: Mar. 12, 1992

Related U.S. Application Data

[60] Division of Ser. No. 557,639, Jul. 30, 1990, Pat. No. 5,147,514, and a continuation-in-part of Ser. No. 388,003, Aug. 2, 1989, abandoned.

[51] Int. Cl.$^5$ .............................................. C07K 3/00
[52] U.S. Cl. .................. 204/157.68; 530/356
[58] Field of Search ................ 204/157.68; 530/356

[56] References Cited

U.S. PATENT DOCUMENTS 3,152,976  10/1964  Kuntz .......................... 204/157.68
4,835,258  5/1989   Hollenberg et al. ............. 530/389.8
5,024,742  6/1991   Nesburn et al. ................. 204/157.68

OTHER PUBLICATIONS

Chemical Abstracts, vol. 72, No. 9, Mar. 2, 1990, p. 24, Abstract No. 38990x, Columbus, Ohio, US; C. Gowri, et al., "Photooxidation of collagen in the presence of methylene blue", Leather Sci. (Madras) 1969, 16(8), 297–300.

Primary Examiner—T. Tung
Assistant Examiner—C. D. Muirheid
Attorney, Agent, or Firm—Vaden, Eickenroht, Thompson, Boulware & Feather

[57] ABSTRACT

The present invention relates to a process for cross-linking a proteinaceous material. The process comprises: i) soaking the material to be cross-linked in an agueous solution of high osmolality; ii) incubating the material in an agueous buffer including an amount of a photooxidative catalyst sufficient to catalyze photooxidation of the material; and iii) irradiating the material and the catalyst of step (i) with light that includes a range of wavelengths selectively absorbed by the catalyst. Irradiation is effected under conditions such that cross-linking of the material occurs. In a further embodiment, the present invention relates to a cross-linked product produced by the above-described method.

9 Claims, 1 Drawing Sheet

CROSS-LINKING COLLAGENOUS PRODUCT

CROSS REFERENCE TO RELATED APPLICATION

This application is a divisional of copending application Ser. No. 07/557,639, filed Jul. 30, 1990, now U.S. Pat. No. 5,147,514, a continuation-in-part of my copending application Ser. No. 07/388,003, now abandoned filed Aug. 2, 1989 and entitled "A Process for Cross-Linking Proteinaceous Material and the Product Formed Thereby".

TECHNICAL FIELD

This invention relates, in general, to a process for cross-linking and stabilizing proteinaceous material, and in particular, to a process for photooxidizing collagenous material in the presence of a photo-catalyst to cross-link and stabilize that material. The invention also relates to the resulting cross-linked product.

BACKGROUND OF THE INVENTION

Reagents and processes currently used for protein cross-linking generally depend upon the incorporation the cross-linking reagent into the protein matrix to cross-link the $\epsilon$-amino groups of lysine, hydroxylysine, and/or other groups in the protein. Common cross-linking reagents in such processes include formaldehyde and glutaraldehyde; other processes include the introduction of a phthaloyl or adipoyl moiety into the protein via phthaloyl dichloride adipoyl dichloride, respectively, and/or the introduction of a mercaptan for oxidization to a disulfide bond.

The cross-linking processes, reactions and reagents the prior art vary, but most involve incorporating the reagent into or around the protein. For example, recent data by Cheung and Nimni (Connec. Tissue Res. 10:201 (1982) and Connec. Tissue Res. 13:109 (1984)) on the cross-linking reagent glutaraldehyde indicate that when this reagent is used to treat collagen fibrils, for example, a polymeric-like coating forms around the fibrils, resulting in stiffer collagen matrix.

In contrast, the cross-linking method disclosed and claimed herein does not depend upon the incorporation of a cross-linking reagent into the material to be cross-linked or the coating of the material with a cross-linked reagent. The present process involves the use of a photooxidative dye which acts as a cross-linking oxidation catalyst or promotor and which can be removed from the cross-linked product.

The use of photooxidative catalysts in various photooxidation processes has been previously reported (see e.g., Ray, Method in Enzymol. 11:490 (1967); Westhead, Biochem 4:10 (1965); Ray and Koshland, Jr., J. Biological Chem. 18:409 (1967); and Foote, Science 162:3857 (1968). However, they do not appear to have been used for cross-linking proteinaceous materials. For instance, Ray and Koshland, Jr., supra, used methylene blue and Light to photooxidize the enzyme phosphoglucomutase in an attempt to identify the amino acid residues of that protein which are essential to the activity of the enzyme by selective destruction of amino acids. Likewise, Westhead, supra, inactivated yeast enolase by photooxidation of histidine residues with the dye rose bengal.

Excitation of a dye by light has also been used to covalently couple the dye to a protein (Brandt, et al., Biochemistry 13: 4758 (1974)), and that technique has led to a method of dye-sensitized photolabeling of proteins (Brantit, et al., Anal. Biochem. 93:601 (1980). Although the technique is useful for such purposes as the study of the molecular arrangement of proteinaceous membrane components (Id.) and protein conformation (Hemmendorff, et al., Biochem. Biophys. Acta 667: 15 (1981)), the technique does not appear to introduce inter- and/or intra-molecular cross-links into the protein matrix.

A dye-catalyzed process said to be useful for preparing thermostable, irreversibly cross-linked collagenous polymers is described in U.S. Pat. No. 3,152,976. This patent alleges that the product resulting from that process is characterized by certain physical-chemical properties similar to those obtained by prior art tanning processes. However, the subsequent data presented in that patent do not support a conclusion that the product of that process possesses the properties of products of prior art tanning processes which would make that product a useful biomaterial for such applications as vascular grafts, heart valves, pericardial patches, injectable collagen, or replacement ligaments or tendoils. Instead, that reference states that the product is more susceptible to enzymatic degradation than "uncrosslinked" collagen. Such results are, of course, totally contrary to the use of such a product as, for instance, a heart valve (imagine a heart valve digested by even tile mildly proteolytic enzyme papain in hours, or even seconds, as described in Example VII of that reference). These seemingly anomalous results can perhaps in part be explained by the apparent motivation for making the invention described in that patent, namely the formation of "shaped articles" such as sponges or fibrils (sutures?), ostensibly of a type which can be implanted in the body without type need for subsequent removal.

The results reported in the '976 patent can perhaps also be explained by a close examination of the process described therein. For instance, the reference describes the preparation of a "starting material" on which the process set out in that patent is conducted by dispersing collagenous material in aqueous acid solution. Acid has the well-known effect of denaturing the protein comprising the collagen fibril. It is, of course, the three-dimensional structure of the proteins comprising the collagen fibril which imparts to the fibril the unique properties of collagen; change that structure and the protein cannot interact in the manner needed to give rise to those properties. A further explanation for the results described in that patent is suggested by P. H. von Hipple, "Structural and Stabilization of the Collagen Molecule in Solution" (in Treatise on Collagen, Vol. 1: Chemistry of Collagen, G. N. Ramachandran (Ed.), London: Academic Press Inc. (London) Ltd. (1967), pp. 253–338 at 262), reporting that collagen molecules extracted by acid and neutral salt procedures differ in the extent to which they are covalently cross-linked, size, shape, interaction properties and rate of fiber formation. Although based on preliminary data such that the author was careful to point out that results had been reported by other investigators which did not show any differences, subsequent experimentation supports the existence of such differences.

In light of this prior art, it was surprising to find that photooxidation of a protein in the presence of a photocatalyst and sufficient oxygen, under controlled conditions of pH and temperature, cross-linked and stabilized the collagen to, for instance, enzymatic degradation, without stiffening the matrix like in conventional tanning processes.

OBJECTS OF THE INVENTION

An object of this invention is to provide an effective and efficient method for tile non-specific cross-linking of proteinaceous materials.

A further object of this invention is to provide a stable cross-linked product.

A further object of this invention is to provide a collagenous product, and a method of making that product, having physical-chemical properties which make that product suitable for use as a biomaterial for use as an artificial tendon, heart valve, or pericardial patch.

A further object of this invention is to provide a product, and a method of making that product, which is not antigenic when implanted in a mammal.

A further object of this invention is to provide a product, and a method of making that product, which does not calcify when implanted in a mammal.

A further object of this invention is to provide a product, and a method of making that product, which is not cytotoxic when implanted in a mammal and over which endothelial cells are capable of growing.

Other objects of the invention, as well as the several advantages of the invention, will be apparent to those skilled in the art upon reading the specification, the examples and the appended claims.

SUMMARY OF INVENTION

In accordance with the present invention, a process is disclosed whereby proteinaceous material is efficiently and effectively cross-linked and stabilized by subjecting such material to photooxidation in the presence of a photo-catalyst. In one embodiment, the present invention relates to a process for cross-linking proteinaceous material which comprises: i) soaking the material to be cross-linked in an aqueous buffer of high osmolality; (ii) incubating the material in an aqueous solution including sufficient photooxidative catalyst to catalyze the formation of inter- and intramolecular cross-links by oxidation of the material; and ( iii ) irradiating the material and the catalyst of step (i) with light that includes a range of wavelengths selectively absorbed by the catalyst. Irradiation is effected under temperature and pH conditions, and an oxygen concentration, such that cross-linking of the material occurs. The present invention also relates to a cross-linked proteinaceous product produced by the above-described method.

The process of tile present invention provides cross-linked, stabilized proteinaceous products which are suitable biomaterials for use in tile replacement and/or repair of diseased or damaged body tissues (medical prosthetics ). When so used, the products of the present invention are superior to products previously employed, for they retain the mechanical properties of the pre-treated material, that is, they remain supple and plaint. In addition, the product is non-immunogenic.

The product of the present invention is further advantageous in medical prosthetics due to its stability. The cross-linked product resists in vivo degradation and calcification when implanted. Therefore the cross-linked product of the present invention is superior to tile biomaterials known in the art which are susceptible to ordinary proteolytic degradation and mineralization.

DETAILED DESCRIPTION OF THE INVENTION

Figure 1:
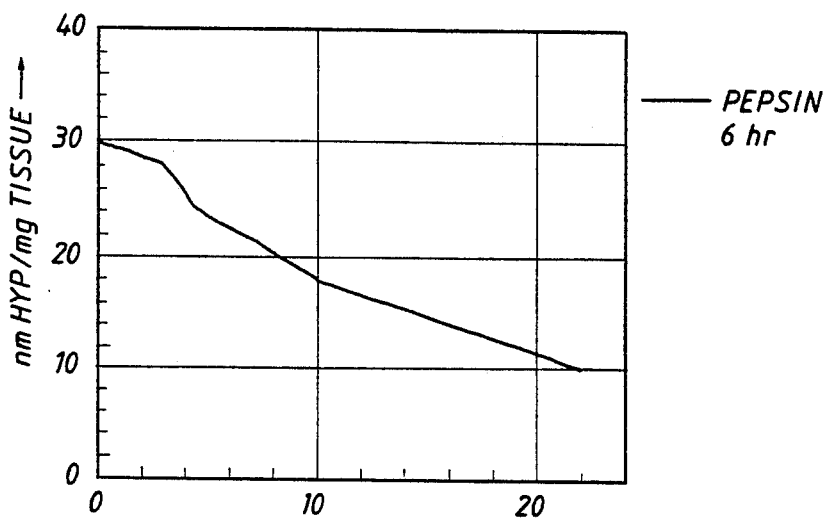
FIG. 1—Effect of catalyst/irradiation on protein cross-linking and stability as measured by the susceptibility of tissue samples to pepsin digestion.

The process of the present invention provides an efficient and effective method for cross-linking and stabilizing various proteinaceous materials including, but not limited to, collagen, collagen fibrils and collagen matrices. The term proteinaceous material as used herein includes both proteins such as collagen and protein-containing materials such as tissues. As a general rule, the particular proteinaceous material utilized as the starting material is determined by the intended use of the product and for that reason, the process of the present invention has particular utility for cross-linking collagenous materials. For instance, if it is desired to build a heart valve from the product of the process of the present invention, the preferred starting material is a material having a high collagen content such as the pericardium, for instance, bovine pericardium, if the cross-linked product is to be used as a vascular graft, such starting materials as the aortic arch of rats or other relatively small animals or the carotid artery of pigs, sheep, or cows are used to advantage. To make injectable collagen, finely ground reconstituted bovine skin collagen is used. The material to be cross-linked can also be provided as a tissue sample. Such materials are harvested from the donor animal and immediately immersed in cold buffered saline for storage, with frequent rinses and/or changes with fresh saline, until processed in accordance with the process described hereinor solubilized or suspended if finely ground. However, any proteinaceous material containing tyrosine, tryptophan, and/or histidine residues is suitable for cross-linking by the present process.

The proteinaceous material to be photooxidized is then immersed, dispersed, or suspended (depending upon its previous processing) in an aqueous media for processing in accordance with the present invention. Suitable media for immersion of the proteinaceous material (for purposes of convenience, the word "immersion" shall be considered to include suspension and/or solubilization of the proteinaceous material) include aqueous and organic buffer solutions having a neutral to alkaline pit, preferably a pH of about 6.5 and above because of the denaturation caused by acid pH. Particularly preferred are buffered aqueous solutions having a pH of from about 6.8 to about 8.6. Examples of media that can be used herein include:

1. water or low ionic strength buffers;
2. phosphate buffered saline;
3. high ionic strength buffers ($\mu=1.75-3.0$); and
4. organic buffers containing potassium or sodium phosphate, or potassium or sodium chloride, such as a Good's buffer (e.g., HEPES, TES or BES-Research Organics, Inc.)

The media may also contain tile photocatalyst, which is preferably soluble therein.

In a particularly preferred embodiment, two media solutions are utilized for what is referred to herein as "preconditioning" the collagenous material before irradiation. The material is "preconditioned" in the sense that materials soaked in the first media solution and irradiated in the second are apparently bettea: cross-linked, e.g., they show improved mechanical properties and decreased susceptibility to proteolytic degradation. The efficacy of this preconditioning is affected by the osmolality of tile first media solution, it being preferred that solutions of high osmolality be used as the first media solution. Particularly preferred are sodium potassium, or organic buffer solutions such as sodium, chloride, sodium phosphate, potassium chloride, potassium phosphate, and Good's buffers having a pit of from about 6.8 to about 8.6, the osmolality of which have been increased by addition of a solute such as 4M sucrose or other soluble, high molecular weight carbohydrate to between about 393 mosm and about 800 mosm.

The solute added to increase the osmolality of the first media appears to have an adverse effect on the degree of cross-linking of the product when present during irradiation. Consequently, after soaking in the first media, collagenous materials are preferably removed therefrom and immersed in a second media for irradiation. The second media is preferably an aqueous buffered solution having a pH of from about 6.8 to about 8.6 in which the photo-catalyst is dissolved. Preferred second media are sodium and potassium phosphate buffers having a pH of from about 7.4 to about 8.0 and an osmolality of from about 150 to about 400 mosm, $300 \pm 10$ mosm being particularly preferred.

When the material to be cross-linked is a piece of tissue, tendon, or pericardium, that sample is advantageously immersed sequentially in the first media and then in the catalyst-incorporated second media prior to photooxidation for a total period of time sufficient to allow tissue, dye, and medium to reach equilibrium. When the ratio of the concentration of the medium to that of the material to be cross-linked is in the range of from about 10:1 to 30:1, equilibrium can generally be readily achieved. The ratio of the concentrations is generally not critical, and may be adjusted up or down as desired. Once an equilibrium is reached, the sample is photooxidized in the catalyst-incorporated medium. The time required to reach equilibrium varies depending upon such factors as, for instance, the temperature of the media solutions, the, osmolality of the first media, and the thickness of the tissue or other sample of proteinaceous material. A period of time as short as a few mixtures or as long as several days may be sufficient, but it has been found that periods of from minutes to hours duration is generally sufficient to allow sufficient time for most collagenous materials and media to equilibrate.

Generally speaking, the suitability of a catalyst for use in the present process is dependent upon the ability of the catalyst to be sensitized into an exited state (T.) where it serves as a photosensitizer. The substrate then reduces the (T.) state of the sensitizer by electron transfer. Studies have provided evidence that the substrate reacts initially with triplet state catalyst, producing secondary reactive radicals by electron or H atom transfer reactions. See, Spikes and Straight, Ann. Rev. Phys. Chem. 18:409 (1967).

The catalysts contemplated for use herein are photooxidative catalysts (photo-catalysts) that when activated will cause transfer of electrons or hydrogen atoms and thereby oxidize a substrate in the presence of oxygen. Although varied results are possible depending upon the particular catalyst utilized, appropriate catalysts include, but are not limited to, those listed in Oster, et al., J. Am. Chem. Soc. 81: 5095, 5096 (1959). Particularly preferred catalysts include methylene blue, methylene green, rose bengal, riboflavin, proflavin, fluorescein, rosin, and pyridoxal-5-phosphate.

The concentration of catalyst in the media will vary based on several process parameters, but should be sufficient to insure adequate penetration into the material to be cross-linked and to catalyze the photooxidation of the protein. A typical catalyst concentration ranges from about 0.0001%–0.25% (wt/vol); the preferred concentration ranges from about 0.01 to about 0.1%.

To achieve maximum cross-linking and stabilization of the proteinaceous product, the following steps should be taken: (1) the photooxidative catalyst should be completely solubilized in the reaction medium prior to use to ensure that the desired dye concentration is achieved; (2) the concentration of the catalyst in the tissue or suspension should be in equilibrium with that in the surrounding medium; and (3) the catalyst solution should be filtered to remove any sizable particulate matter, including chemical particulates, therefrom.

Because the present process involves primarily an oxidative reaction, to assure completion of the reaction, an adequate supply of oxygen must be provided during photooxidation. While an oxygen concentration of about 20% by volume (referring to the concentration of oxygen in the atmosphere over the media) is preferred to assure sufficient dissolved oxygen in the media to prevent oxygen content from becoming rate limiting, concentrations >0% and ranging up to 25% can also be used. Depending upon the temperature at which the proteinaceous material is held during exposure to light, the oxygen requirement can be met, for instance, by agitating the solution or otherwise mixing the solution, suspension, or sample during the reaction process. Oxygen concentration in the atmosphere over the media during irradiation is preferably maintained in the range of from about 5% to about 20%. Such concentrations (again depending upon temperature) can also be achieved, for instance, by bubbling air into the media during irradiation of the proteinaceous material or, if concentrations higher than about 20% are desired, by bubbling oxygen mixtures or air having an increased oxygen content into the media.

As with other catalytic or kinetic-type reactions, the temperature at which the reaction is run directly affects the reaction rate and the oxygen available in the media. Tests conducted with various media ranging in pH from about 6.8 up to about 7.4 and having an osmolality of $300 \pm 10$ mosm indicate that as the temperature of the media increases from about 4° C. to about 50° C., oxygen concentration drops in roughly linear fashion from about 11–12 ppm to about 5 ppm. The dye-catalyzed photooxidation process of the present invention is exothermic, and it is, therefore, preferred that a relatively constant temperature be maintained during irradiation of the proteinaceous material to prevent denaturation of the proteinaceous material and the driving of the oxygen out of the media by the increase in temperature. Usually, a recirculating bath is sufficient to maintain and control the temperature within the jacketed reaction vessel or chamber but placement of the reaction chamber within a controlled environment such as a refrigerator or freezer will work as well. As disclosed herein, photooxidation conducted at temperatures ranging from about −2° C. to +40° C. has been shown to be effective; the preferred temperatures are from about 0° to about 25° C. To prevent or alleviate denaturation of the protein comprising the proteinaceous material, temperatures below the denaturation temperature of that protein are preferred. Likewise, temperatures above the freezing point of the reaction medium are also preferred.

It is the combination and/or interaction of the variables of temperature, pH, and oxygen concentration described herein which is believed not to have been previously identified as critical in photooxidative cross-linking. Hence, the process of the present invention is conducted at temperatures low enough to avoid heat denaturation and pH high enough to avoid acid denaturation of the collagen or other proteinaceous material during cross-linking. Likewise, temperature is held at a level sufficient to maintain the oxygen concentration in the media in which the proteinaceous material is immersed during irradiation.

Once the solution, suspension, or sample is prepared, it is photo-irradiated, preferably in a controlled system wherein temperature, distance to light source, irradiation energy and wavelength, oxygen concentration and period of irradiation can be monitored and/or maintained. The solution, suspension, or sample of proteinaceous material is photo-irradiated under conditions sufficient to cause cross-linking. Photooxidation is generally achieved using incandescent, white light or fluorescent light, i.e., visible light, or that portion of light in the visible range that is absorbed by the catalyst. Inexpensive light sources such as household bulbs, fluorescent lights and flood lamps are suitable for use herein.

The intensity of the light employed, and the length of time required to cross-link a given proteinaceous material will vary depending upon several factors. These include: (1) the type and amount of proteinaceous material; (2) the thickness of the tissue sample; (3) the distance between the proteinaceous material and the irradiation source; (4) the catalyst employed; (5) the concentration of catalyst; and (6) the type and intensity of the light source. For instance, exposure time may vary from as little as a few seconds up to as much as about 160 hours. With regard to the intensity of the light, one or more lights may be used of intensity preferably ranging up to about 150 watts, preferably held at a distance from about 2.5 cm to 12 cm from the sample surface. Greater exposure time is required when fluorescent or lower power lights are utilized. These ranges are quite variable; however, they may be easily determined for a given material without resort to undue experimentation using the disclosure and examples provided herein as a guide. In a presently preferred embodiment, the intensity of the light and the exposure time is conveniently expressed in lumen hours, and when common fluorescent lights are used as the light source, a range of from about 100 to about 20,000 lumen hours is utilized for cross-linking most samples of proteinaceous material.

Evidence of the cross-linking of proteinaceous material by photooxidation in the presence of a catalyst in accordance with the process of the present invention is provided by several tests. For instance, polyacrylamide gel electrophoresis of the irradiated material in sodium dodecylsulfate (for example, 0.1%) evidences such cross-linking by a significant decrease in the amount of lower molecular weight material with the simultaneous appearance of high molecular weight material. While amino acid analysis of hydrolyzates of cross-linked proteinaceous material demonstrates a paucity of methionine, tyrosine and histidine (all destroyed by photocatalytic oxidation), this reduction is not necessarily evidence of cross-linking. For example, if collagen is treated with $KI/I_2$ solution, derivatization of tyrosine and histidine occur, essentially eliminating these amino acids from an amino acid profile without cross-linking, as evidenced by the lack of change in the gel electrophoretic patterns.

Further evidence of cross-linking is provided by solubility and digestibility tests such as those set forth in the examples that follow. For instance, cross-linked collagen is generally insoluble such that solubility tests provide direct evidence of the degree of cross-linking. The digestibility tests involve incubation of the proteinaceous product with a proteolytic enzyme such as papain, trypsin, pepsin, or bacterial collagenase, and the subsequent testing of the media in which the product and enzyme are incubated for soluble degradation products of tile cross-linked product. The test is generally accomplished by pelletizing the undigested, cross-linked product and the enzyme by centrifugation and testing the resulting supernatant for degradation products. The latter is particularly useful in light of the destruction of the amino acid histidine by photooxidation; analysis of the supernatant for histidine content and a comparison of that content to the amount of an amino acid such as hydroxyproline, which is not destroyed by photooxidation, in the supernatant provides a particularly sensitive assay for the degree of cross-linking. This comparison can be advantageously expressed as a ratio of histidine to hydroxyproline (his/hyp ratio), higher his/hyp ratios being indicative of more effective cross-linking.

The process disclosed herein is carried out in a batch, intermittent, or continuous manner. Following photo-irradiation, the cross-linked product is advantageously subjected to various treatments for the removal of the catalyst and other chemicals or impurities found therein before being used as a vascular graft, heart valve leaflet, or other uses listed above. Multiple rinses in a fresh buffer solution are, for example, used, followed by a least partial de-watering with, for instance, ethanol. The number of rinses and the volume of rinse solution required depends upon the mass of the tissue or the suspended material and the catalyst concentration utilized.

The following non-limiting Examples describe the invention in further detail.

EXAMPLE 1

Pure Collagen Fibrils Cross-linked at 18 C.

Pure reconstituted soluble bovine skin collagen fibrils (0.25 grams) were mixed and suspended in 0,065 liters of 0.02 M sodium phosphate buffer, pH 7.4, containing 0.01% (wt/vol) methylene green. The collagen fibrils were irradiated in a jacketed water bath maintained at 18° C. A thermometer was placed in the reaction vessel to monitor the temperature. Two 150 watt floodlights held about 6 cm or 2.4 inches from the suspension surface were turned on and the temperature in the reaction vessel began to rise indicating that possibly (1) an exothermic reaction was taking place and/or (2) light energy was being absorbed by the catalyst in the medium causing an elevation in the temperature of the suspension.

The lights remained on and the reaction was allowed to continue for four hours. The temperature reached an initial maximum of 45° C. which was then reduced to, and maintained at about 18° C. for the remainder of the reaction period. The oxygen concentration in the reaction medium was held at a level sufficient to insure adequate oxygen in the media by keeping the reaction vessel open to the atmosphere while stirring the reaction mixture vigorously.

The disclosed process was deemed to be effective in cross-linking proteinaceous material when neither heating of the collagen product to 65° C. (which would denature and solubilize the naturally cross-linked native collagen), nor digestion with pepsin at 15° C. (which would also solubilize the native collagen) was successful in breaking it down. No denaturation of the collagen product was observed.

EXAMPLE 2

Pure Collagen Fibrils Cross-linked at 0° C.

Following the procedures set forth in Example 1, several samples containing approximately 0.25 grams of pure reconstituted bovine skin collagen fibrils were mixed and suspended in 0.065 liters of 0.02 M sodium phosphate buffer, pH 7.4, containing 0.01% (wt/vol) methylene green. Photo-irradiation of the suspensions was carried out in jacketed water baths maintained at a temperature of 0° C. Two 150 watt floodlights held about 6 cm or 2.4 inches from the surface of each suspension were turned on and the reactions were allowed to run for periods up to 6 hours. The oxygen concentration in the vessels was maintained at sufficient levels by keeping the reaction vessels open to the approximately 20% oxygen concentration of the atmosphere and by stirring (see Example 1).

Photooxidation of the samples was stopped at various time intervals during irradiation and pepsin digestion was employed to test the cross-linking and stability of the resulting products. in none of the samples was any significant degree of solubilization achieved. Even dilute acetic acid at 100° C. or digestion with 5% pepsin (enzyme: substrate) at temperatures up to 18° C. did not achieve degradation of the cross-linked collagen product.

EXAMPLE 3

Cross-linking of Reconstituted Soluble Collagen Fibrils

Soluble collagen was extracted from 2 year-old bovine skin and purified. Purified reconstituted soluble collagen fibrils were irradiated under the conditions described in Example 2 in 0.01% and 0.1% catalyst for 6, 16, 24, and 48 hours. Attempts were made to dissolve 0.4 mg samples of the reconstituted soluble collagen fibrils at room temperature after they were cross-linked in 0.25 nil of 0.5 M acetic acid as well as in 0.250.ml of 0.1 M TRIS-borate buffer pit 8.6 containing 4 M urea and 0.2% SDS. The control (non-cross-linked) fibrils dissolved readily at 0° C. and rapidly at room temperature in the latter two solutions. The collagen suspensions failed to dissolve when heated to 65° C. Some of these suspensions were subjected to PAGE analyses. The reconstituted soluble collagen (non-crosslinked) fibrils that dissolved showed normal electrophoretic patterns. However, when the supernatents of the heated cross-linked fibrils were run on the gel, the electrophoretic patterns were extremely light and barely visible.

Pepsin and collagenase treatments were used to assess the efficiency of the cross-linking reaction. There was apparently very little if any dissolution caused by the pepsin digestion. There was some precipitate left after collagenase treatment. Aliquots of the supernatents and residues from each were collected and hydrolyzed. Other aliquots were removed for PAGE analysis. The residues from the pepsin digestions were insoluble in the TRIS-Borate buffer described above at 65° C.

EXAMPLE 4

Cross-linking Bovine Pericardium Tissue

Using a modified water jacketed reaction vessel similar to that employed in Example 1, a number of samples of bovine pericardium measuring approximately 2 cm$^2$ were irradiated simultaneously with two 150 watt floodlights held 7 cm to 10 cm or about 2.8 to 4 inches from the samples. Individual samples were removed from the vessel after periods ranging from 2.5 to 22 hours of irradiation.

In a first series of experiments, the cross-linking medium consisted of 4.0 M sodium chloride with a $\mu=0.164$ sodium phosphate buffer (pit 7.4) containing 0.1% (wt/vol) methylene green. The tissue samples were equilibrated with the above solution, placed in the apparatus with the medium which was continuously stirred using a magnetic stirrer. The reaction vessel was then irradiated while temperature of the medium was held at about 0° C. After various periods of time, the tissue samples were removed from the media and decolorized by soaking in $\mu=0.164$ sodium phosphate buffer (pH 7.4) until the samples were substantially free of the catalyst.

To test the effect of the catalyst and the irradiation separately, and the catalyst/irradiation combination on tissue, control samples containing no catalyst or catalyst but no irradiation were run in the above reaction. After washing for 12 days, changing wash solution three times per day, with 0.1 M $NH_4HCO_3$, pH 7.9, 0.001 M $CaCl_2$ solution, the cross-linking and stability of the resulting protein products were evaluated based on the susceptibility of the tissue samples to pepsin digestion in a 1% pepsin solution in 3% acetic acid at 4° C. for 24 hours. Reaction of the samples with the enzyme was performed for varied periods time. The results are depicted in FIG. 1.

Typically, tissue samples irradiated for from 2.5 to 22 hours in tile presence of the methylene green showed significant decreases in the solubility of the protein ass compared to the controls. Moreover, a 6 hour pepsin digestion of the control tissue yielded approximately 30 nM hydroxyproline (hyp) per mg of tissue, while the same digestion on a tissue sample irradiated for 22 hours in the presence of methylene green yielded values as low as 10 nM per mg. Clearly the disclosed process successfully cross-linked and stabilized the collagen.

EXAMPLE 5

Effect of Reduced Tissue/Volume of Catalyst

Figure 2:
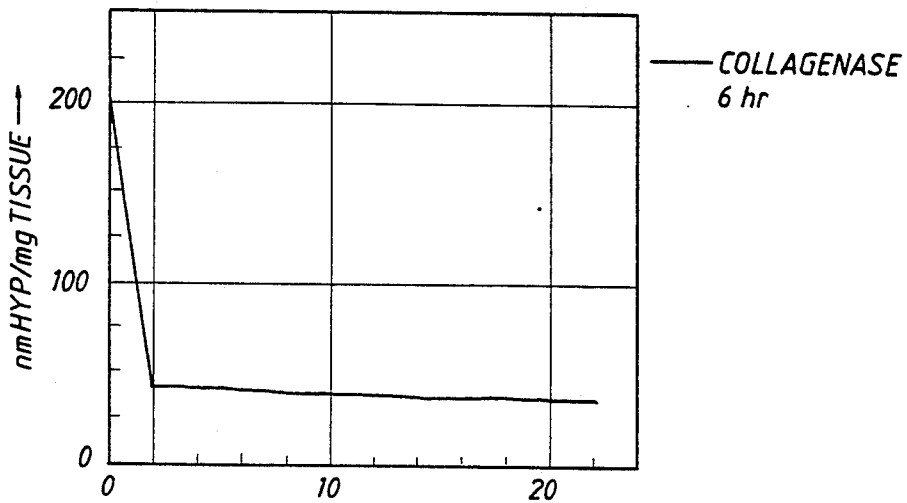
FIG. 2—Effect of catalyst/irradiation on protein cross-linking and stability as measured by the susceptibility of tissue samples to collagenase digestion.

Samples of bovine pericardium were soaked in 3.0 M KCl, $\mu=0.167$ potassium phosphate buffer and then fewer pieces of pericardium than utilized in Example 4 were placed in that same buffer including 0.1% methylene green under the same reaction conditions as described in Example 4 and exposed to light for up to 22 hours in these experiments, digestion with pure bacterial collagenase (1% collagenase solution in 0.15 M TES buffer, pH 7.5 in 0.001 M CaCl$_2$ at 37° C. for 6 hours) was used to evaluate cross-linking and stability. The control sample yielded 206 nM hyp per mg of tissue, whereas the sample irradiated for 22 hours yielded 36 nM of hyp per mg of tissue. These results are depicted in FIG. 2. The reduced tissue susceptibility to collagenase digestion demonstrated the successful stabilization of the tissue.

EXAMPLE 6

Cross-Linking of Soluble Collagen Fibrils

Soluble collagen was prepared by extraction of two-year old bovine corium with 1% acetic acid. The soluble collagen was purified by salt precipitation from the acetic acid solution and two low ionic strength dialyses from the acetic acid solution, dissolved in 1% acetic acid, and reconstituted into fibrils by dialysis against 0.02 M sodium phosphate buffer, pH 7.4. Aliquots of the reconstituted collagen were immersed in 0.02 M sodium phosphate buffer, pH 7.4 containing 0.01% methylene green in aluminum-foil covered flasks. The flasks were held at 4° C. in a water bath while bubbling atmospheric air therethrough under two 150 W flood lamps for 24 hours at a distance of about 3 cm and the foil removed from a selected number of flasks.

Fibrils from irradiated and non-irradiated aliquots were dialyzed against 0.02 M sodium phosphate buffer, pH 7.4 to remove the dye and then centrifuged and placed in 3% acetic acid. The non-irradiated fibrils dissolved in the acetic acid while those that were irradiated remained insoluble, even after heating to 65° C., indicating that the irradiated fibrils had been effectively cross-linked. When the supernatent from the irradiated fibrils was hydrolyzed for hyp content, none was found, confirming the cross-linking of the collagen.

Fibrils from irradiated and non-irradiated aliquots were also dialyzed for seven days with three changes per day against the same sodium phosphate buffer until free of catalyst. A few grams of DOWEX 50 X8 resin (20-50 mesh) in the H$^+$ form was included with the dialyzing fluid to absorb the catalyst. Samples of each irradiated and non-irradiated fibrils were then hydrolyzed with 6 N hydrochloric acid for 24 hours at 110° C. in vacuo. The hydrolysates were dried and about 50 mg at a time was subjected to molecular sieve chromatography on a BIO-GEL P2-400 mesh column (1.6×100) that had been equilibrated with 0.1 M acetic acid ad calibrated with a 5 mg acid hydrolyzate of NA$^3$BH$_4$-reduced collagen fibrils. The column was monitored by taking small aliquots of the fractions and developed color for amino acids by ninhydrin and scintillation counting of the radioactivity. Void volumes (fractions 33 to 48) of natural cross-links of collagen (cross-link fractions) were pooled, lyophilized and subjected to amino acid analysis.

In comparing tile amino acid chromatograms from the irradiated and non-irradiated fibrils, six distinct new peaks appeared in the hydrolyzate from tile irradiated fibrils between phenylalanine and hydroxylysine. Except for histidine (his), this area is usually a blank area in a non-irradiated chromatogram, and the presence of these high molecular weight substances is indicative of the formation of cross-linked amino acids formed by photooxidation with the dye. Further indication was provided by the absence of his in this area, his being destroyed by photooxidation.

EXAMPLE 7

Effect of Increased Osmotic Pressure on Cross-Linking

A rectangular illumination cell was constructed from clear plastic with an outer jacket of the same material and tubes communicating with the inner chamber for circulation of media and dye. A frame, comprised of narrow strips of plastic including spaced holes therealong for suturing tissue samples thereto, was constructed in a size fitting into the inner chamber of the cell. After suturing a piece of bovine pericardium to that frame and inserting the frame into the inner chamber, a media comprised of 2.8 M potassium chloride, $\mu=0.164$ potassium phosphate buffer, pH 7.4, including 50% sucrose, was circulated through the inner chamber of the illumination cell. After soaking in the high osmotic pressure media, the tissue was incubated with the media including methylene green as described in Example 5, above and illuminated for 24 and 48 hours by two 150 watt flood lamps at a distance of about 4.5 cm while holding temperature at between −2° C. and 6° C.

After irradiation, small pieces of tissue from each sample were digested with pepsin or bacterial collagenase as described in Examples 4 and 5. The following ratios of hyp/mg of tissue in enzyme columns clearly demonstrate the cross-linking of the tissue samples.

| Time of Irradiation (hrs.) | Pepsin | Collagenase |
| --- | --- | --- |
| 0 (Control #1) | 26 | 314 |
| (Control #2) | 31 | 314 |
| 24 (Sample #1) | 0 | 410 |
| (Sample #2) | 0 | 290 |
| 48 | 0 | 303 |

Additional tissue samples were further stabilized (without apparent change in their tactile properties, e.g., tissue texture and suppleness) by reduction of the newly formed iminium bonds by immersion in a solution of NaBH$_4$ for one hour as demonstrated by the following hyp/mg ratios:

| Time of Irradiation (hrs.) | Pepsin | Collagenase |
| --- | --- | --- |
| 0 (Control #1) | 26 | 314 |
| (Control #2) | 7 | 208 |
| 24 (Sample #1) | 0 | 180 |
| (Sample #2) | 0 | 170 |
| 48 | 0 | 170 |

For purposes of comparison, when a commercially available pericardial patch prepared by glutaraldehyde tanning was subjected to pepsin digestion at 25° C. and 4° C., ratios of 20 and 16 nM hyp/mg of tissue, respectively, were obtained, and when digested with collagenase at 37° C., 32 and 35 nM hyp/mg tissue ratios were obtained.

EXAMPLE 8

Cross-Linking of Rat Collagen

Soluble BAPN rat type i collagen in 0.5 M HAc was divided into six 4 ml samples and each sample placed in a dialysis bag with 300 mg NaCl (no salt was added to sample 5 and 6). Samples were dialyzed into the high osmotic strength buffer described in Example 7 (samples 5 and 6 were dialyzed into phosphate buffered saline (PBS), p[t 7.4) and 2 ml of 0.2% methylene blue. Samples 2 and 3 were transferred to buffer including 0.1% methylene blue in PBS, sample 4 was transferred to PBS including 0.01% methylene blue, and samples 5 and 6 remained in PBS. Sample 2 was exposed to a 150 watt white floodlight located about 7 inches from the surface of the fluid while holding temperature between about 8 and 12° C for eight hours, samples 3 and 4 were exposed for 24 hours under the same conditions, and samples 5 and 6 were exposed for two hours under the same conditions. All samples were then dialyzed back into the until the solutions were no longer blue and then analyzed by SDS-PAGE as described in Example 3, above. The samples exposed for 24 hours were more cross-linked than those exposed for eight hours, and all samples were more cross-linked than samples 5 and 6.

EXAMPLE 9

Reduced Calcification in Growing Rats

Figure 3:
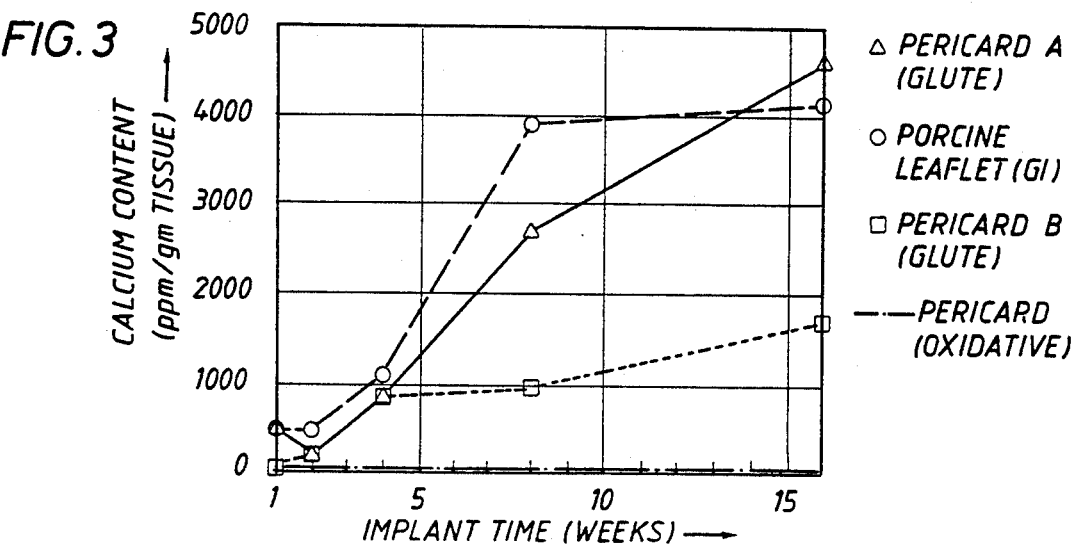
FIG. 3—Calcification of implanted cross-linked tissue. Two glutaraldehyde cross-linked bovine pericardial samples (A and B) are shown (A=X, B=☐), along with glutaraldehyde cross-linked porcine leaflets (0) and a sample of bovine pericardium cross-linked in accordance with the process of tile present invention (--).

Using the conditions described in Example 3, a series of tissues were prepared and implanted subcutaneously into the belly of growing three week old rats. The control tissues were commercially available glutaraldehyde cross-linked bovine pericardium (Pericard-A and Pericard-B) and porcine leaflets (GL). As can be seen in FIG. 3, the tissue treated according to the invention did not significantly calcify as compared to the commercial tissue.

EXAMPLE 10

In vivo Biodegration

Bovine pericardium samples treated as described in Example 3 were implanted subcutaneously into the belly of adult 6 month old rats. Fresh pericardium was used as a control. After three months of implantation, the fresh tissue had resorbed while the treated pericardium remained intact, again demonstrating the cross-linked nature of the collagenous material.

For purposes of completing this disclosure, all of the references cited hereinabove are hereby incorporated by reference. While the present invention has been described in detail for purposes of clarity and understanding, it will be clear to one skilled in the art from a reading of the disclosure that changes can be made in form and detail without departing from the true scope of the invention.

What is claimed is:

1. The stuble cross-linked collagenous product produced by the process comprising the steps of:

soaking a collagenous tissue sample in an aqueous medium;

immersing the soaked sample in an aqueous buffer including a photooxidative catalyst capable of donating electrons to the amino acids comprising the collagen fibrils of the collagenous tissue sample when excited by incident light to form either inter- or intramolecular or inter- and intra-molecular cross-links; and irradiating the soaked sample in an aqueous buffer including the catalyst with light while maintaining the oxygen concentration of the aqueous buffer so as to sensitize the catalyst into an excited state which is reduced by oxidative cross-linking of the amino acids comprising the collagenous tissue sample, the pH being maintained at between about 6.8 and about 8.6 and the temperature being maintained at between about −2° and about 50° C.

2. A stable cross-linked product produced by the method comprising the steps of:

soaking collagen fibrils in a buffered medium having a neutral to alkaline pH which does not denature the collagen fibrils for a period of time sufficient to equilibrate the concentration of collagen with the concentration of a photooxidative catalyst solubilized in the medium, and thereafter oxidizing the collagen fibrils to form cross-linkages therebetween by inducing the transfer of electrons from the photooxidative catalyst to the collagen fibrils in the present of oxygen by exposing the collagen fibrils to light.

3. The product of claim 2 wherein the medium is buffered to a pH of about 7.4.

4. The product of claim 2 wherein the concentration of catalyst ranges from about 0.0001%–0.25% (wt/vol.).

5. The produce to claim 2 wherein the collagen fibrils are photooxidized at a temperature of from about −2° C. to +40° C.

6. The product of claim 2 wherein the collagen fibrils are exposed to light for about 2.5 to about 160 hours.

7. The product of claim 2 wherein the temperature of the medium is maintained at a selected temperature during the time the collagen fibrils are exposed to light.

8. The product of claim 1 wherein the concentration of catalyst ranges from about 0.001%–0.25% (wt/vol.).

9. The product of claim 1 wherein the collagenous sample is exposed to light for about 2.5 to about 160 hours.

* * * * *